(12) United States Patent
Bozzarelli

(10) Patent No.: US 9,622,678 B2
(45) Date of Patent: Apr. 18, 2017

(54) PERINEAL PROBE

(71) Applicant: BEACMED S.r.L., Portalbera (Pavia) (IT)

(72) Inventor: Pier Luigi Bozzarelli, Portalbera (IT)

(73) Assignee: BEACMED S.R.L., Portalbera (Pavia) (IT)

( * ) Notice: Subject to any disclaimer, the term of this patent is extended or adjusted under 35 U.S.C. 154(b) by 135 days.

(21) Appl. No.: 14/521,551

(22) Filed: Oct. 23, 2014

(65) Prior Publication Data
US 2015/0133724 A1 May 14, 2015

(30) Foreign Application Priority Data
Nov. 14, 2013 (EP) .................................... 13192969

(51) Int. Cl.
*A61B 5/0492* (2006.01)
*A61N 1/05* (2006.01)
(Continued)

(52) U.S. Cl.
CPC ........ *A61B 5/0492* (2013.01); *A61B 5/04882* (2013.01); *A61B 5/04884* (2013.01); *A61B 5/4255* (2013.01); *A61B 5/4337* (2013.01); *A61B 5/6852* (2013.01); *A61F 2/0004* (2013.01); *A61N 1/0512* (2013.01); *A61N 1/0524* (2013.01); *A61N 1/36007* (2013.01);
(Continued)

(58) Field of Classification Search
CPC .............. A61B 5/0492; A61B 5/04882; A61B 2018/00553; A61B 2018/00559; A61N 1/0512; A61N 1/0524; A61N 1/36007

USPC ........................................... 600/373; 607/138
See application file for complete search history.

(56) References Cited

U.S. PATENT DOCUMENTS 2,085,644 A * 6/1937 Ferciot ................. A61N 1/0512
607/138
3,800,800 A * 4/1974 Garbe ....................... A61F 5/48
607/138

(Continued)

FOREIGN PATENT DOCUMENTS

| DE | 90 12 750 U1 | 11/1990 |
|---|---|---|
| DE | 94 16 825 U1 | 12/1994 |
| EP | 2 322 110 A1 | 5/2011 |

OTHER PUBLICATIONS

European Search Report for corresponding European Application No. EP 13 19 2969, two pages, completed Mar. 27, 2014.

*Primary Examiner* — Lee S Cohen
(74) *Attorney, Agent, or Firm* — Vorys, Sater, Seymour & Pease LLP

(57) ABSTRACT

Provided is a perineal probe including a substantially cylindrical support rod in an insulating material, defining an axial direction and a circumferential direction, an end portion, constituting the inner end of said support rod, a grip for said perineal probe positioned on the support rod at the opposite end of said end portion, four electrodes positioned on the outer surface of the support rod, wherein each electrode extends for a circumferential portion ranging from 60° to 180°, wherein the electrodes are two by two aligned in an axial direction and reciprocally distanced in a circumferential direction, are in addition two by two aligned in a circumferential direction and distanced in an axial direction, and wherein each electrode is connected to a different electric output.

9 Claims, 4 Drawing Sheets

(51) Int. Cl.
*A61N 1/36* (2006.01)
*A61F 2/00* (2006.01)
*A61B 5/0488* (2006.01)
*A61B 5/00* (2006.01)
*A61B 18/00* (2006.01)

(52) U.S. Cl.
CPC ............... *A61B 2018/00553* (2013.01); *A61B 2018/00559* (2013.01)

(56) References Cited

U.S. PATENT DOCUMENTS

| | | | | |
|---|---|---|---|---|
| 5,385,577 A | * | 1/1995 | Maurer | A61N 1/0512 607/138 |
| 5,452,719 A | * | 9/1995 | Eisman | A61N 1/0512 600/373 |
| 5,456,709 A | * | 10/1995 | Hamedi | A61N 1/0524 607/138 |
| 5,649,976 A | * | 7/1997 | Malewicz | A61N 1/0524 607/138 |
| 2012/0265044 A1 | * | 10/2012 | Broens | A61B 5/04882 600/373 |

\* cited by examiner

PERINEAL PROBE

FIELD OF THE INVENTION

The present invention relates to an improved perineal probe, that is to say an anal or vaginal probe, of the type comprising a substantially cylindrical support rod in an insulating material, defining an axial direction and a circumferential direction, an end portion, constituting the inner end of the support rod, a grip for the perineal probe connected to the support rod at the opposite end of the end portion.

DESCRIPTION OF THE PRIOR ART

As known, various types of perineal probe currently exist used for electro-stimulation for medical purposes, such as in particular re-education for incontinence, or even to detect muscular action potential in said regions.

In particular, the known probes are substantially shaped as cylindrical rods, with a differently shaped end where needed. Said cylindrical rod further comprises electrodes.

In particular a first type of perineal probe, and in particular an anal probe, comprises two electrodes extending along the entire circumference of the cylindrical rod and axially distanced.

Alternatively, a second type of perineal probe, and in particular an anal probe, comprises two electrodes extending axially along lateral portions of the cylindrical rod and axially distanced.

The two types of probe interest the stimulation of different muscle groups.

The prior art described above has several significant drawbacks.

In fact, for each patient a single probe for personal use is needed.

As a result, the patient is obliged to purchase several probes or the physician is forced to apply only one type of treatment.

Moreover, the efficiency and versatility of perineal probes need to be improved.

Another drawback of no less importance is the high production cost of perineal probes which need new moulds for each type of probe.

SUMMARY OF THE INVENTION

In this situation the technical purpose of the present invention is to devise an improved perineal probe able to substantially overcome the drawbacks mentioned above.

Within the sphere of said technical purpose one important aim of the invention is to provide a simple and economical perineal probe.

Another important aim of the invention is to make a versatile perineal probe.

The technical purpose and specified aims are achieved by an improved perineal probe comprising a substantially cylindrical support rod in an insulating material, defining an axial direction and a circumferential direction, an end portion, constituting the inner end of the support rod, a grip for the perineal probe connected to the support rod at the opposite end of the end portion, four electrodes positioned on the outer surface of the support rod, in that each electrode extends for a circumferential portion ranging from 60° to 180°, the electrodes being two by two aligned in the axial direction and reciprocally distanced in a circumferential direction, the electrodes being, in addition, two by two aligned in the circumferential direction and distanced in an axial direction, and each of the electrodes being connected to a different electric output.

BRIEF DESCRIPTION OF THE DRAWINGS

The characteristics and advantages of the invention are clearly evident from the following detailed description of a preferred embodiment thereof, with reference to the accompanying drawings, in which.

DESCRIPTION OF THE PREFERRED EMBODIMENTS

Figure 1:
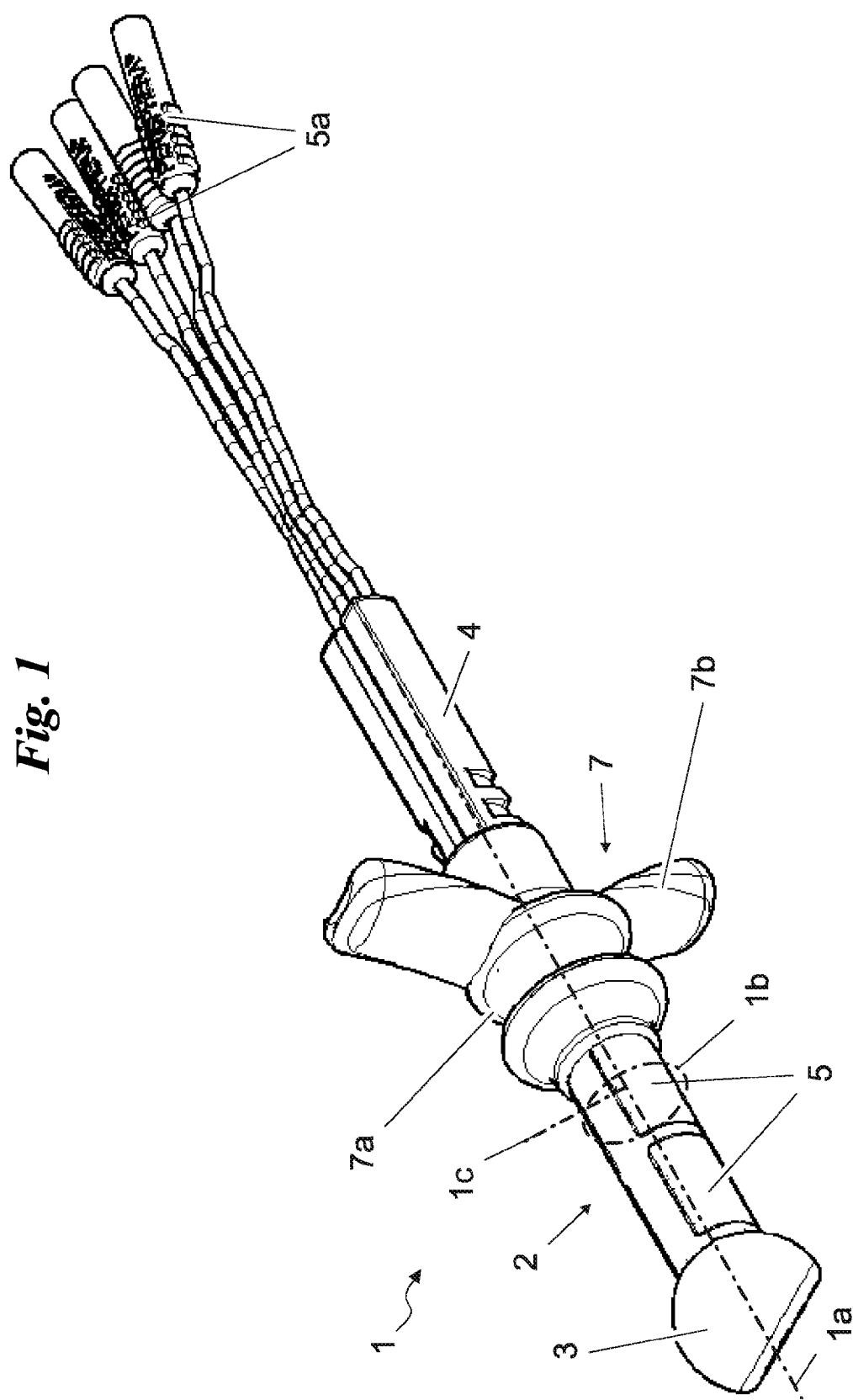
FIG. 1 shows an axonometric view of a first example of perineal probe according to the invention.

With reference to said drawings, reference numeral 1 globally denotes the multivalent perineal probe according to the invention.

Figure 2:
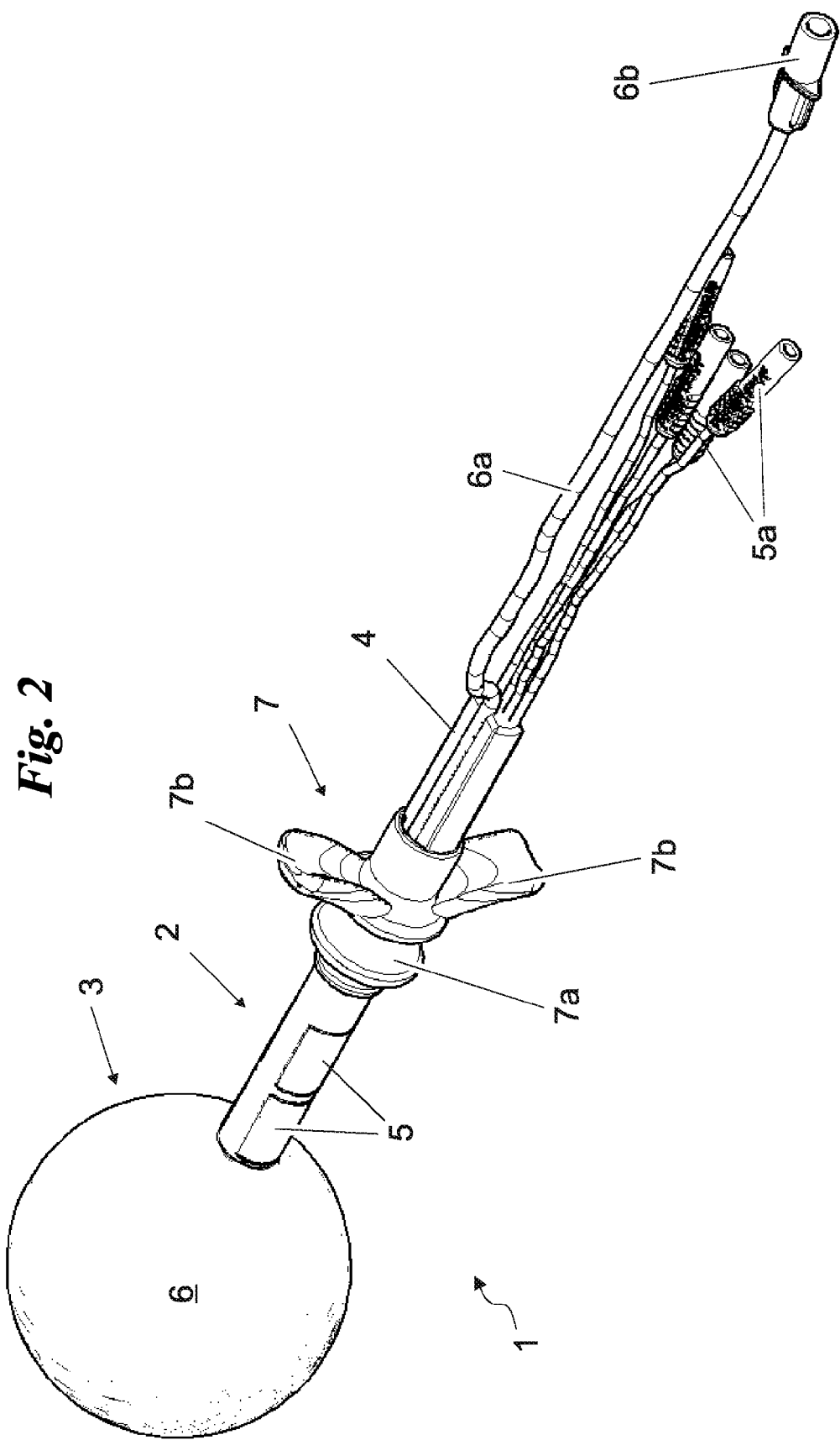
FIG. 2 illustrates an axonometric view of a second example of perineal probe according to the invention.
Figure 3:
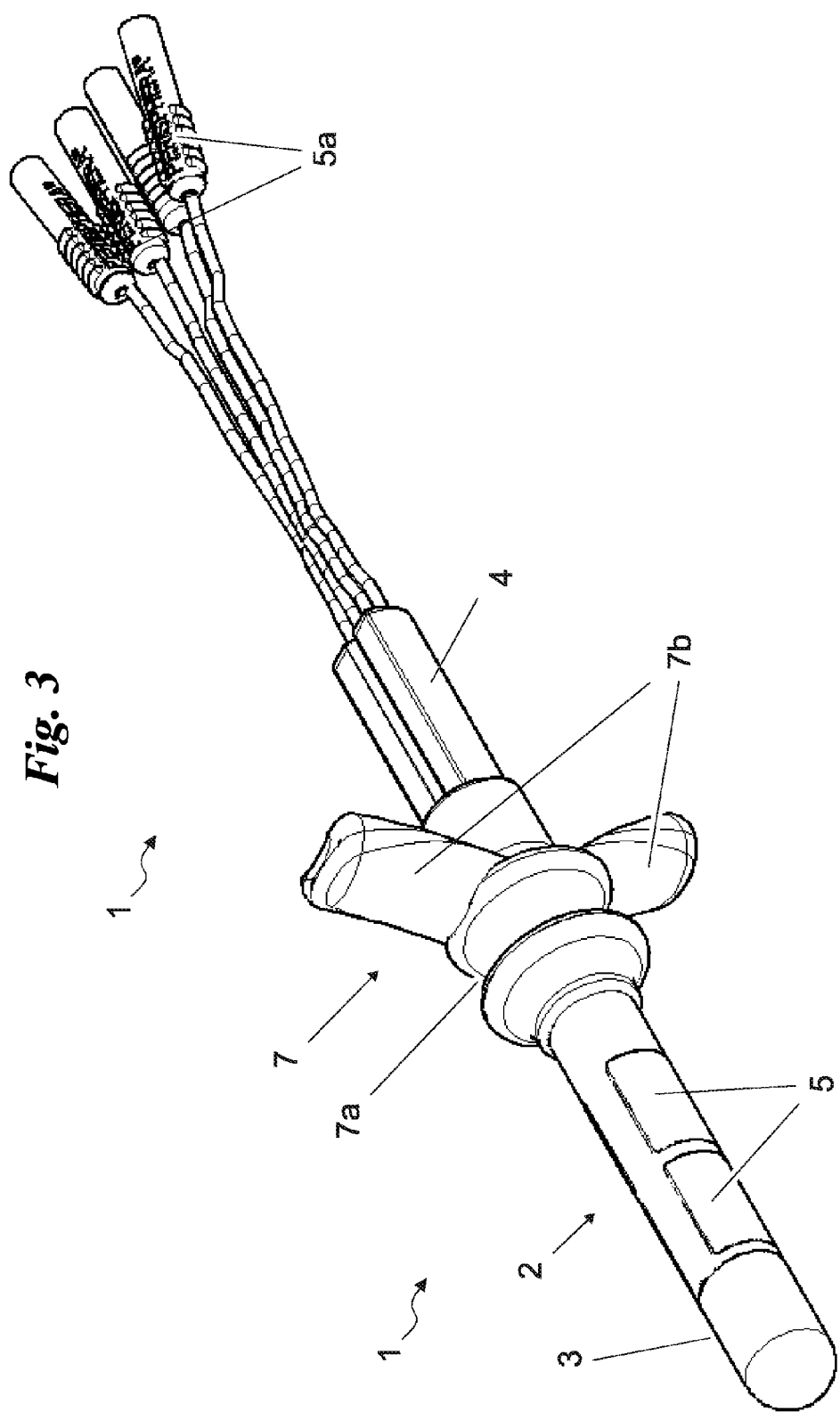
FIG. 3 highlights an axonometric view of a third example of perineal probe according to the invention.
Figure 4:
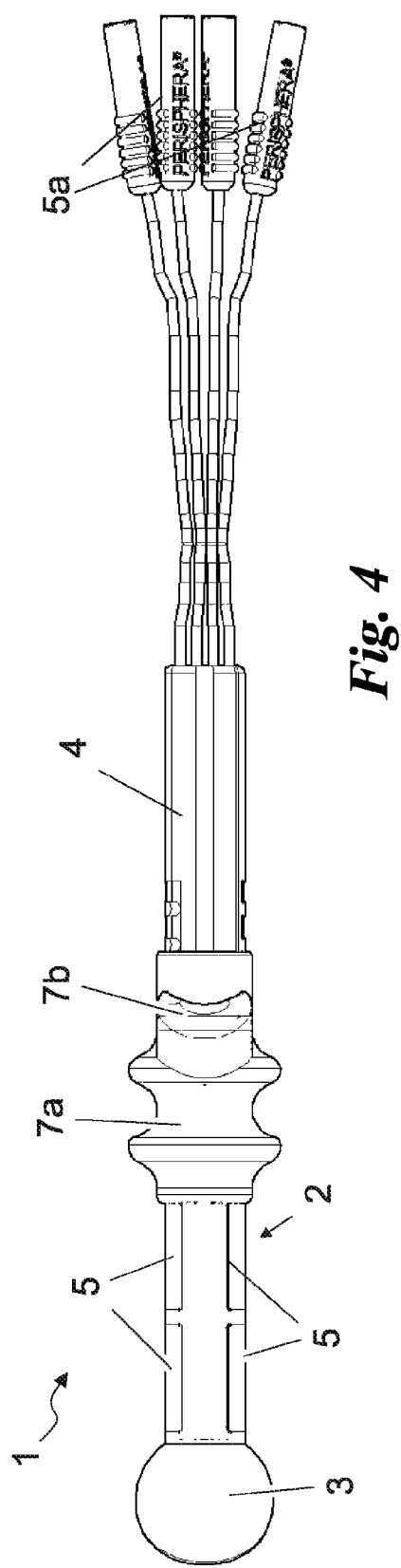
FIG. 4 presents a view from above of the perineal probe according to the invention.
Figure 5:
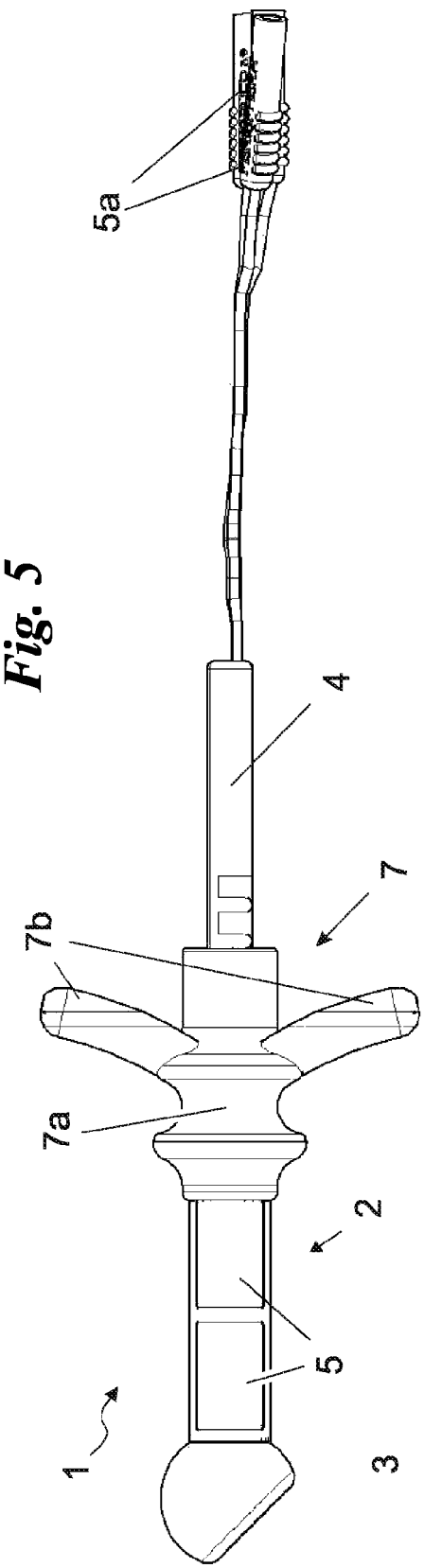
FIG. 5 is a side view of the perineal probe according to the invention.

It is suitable to be used as an anal probe (FIGS. 1 and 2) and as a vaginal probe (FIG. 3). In such latter case in particular for treatment of patients with reduced or compromised vaginal access (vaginismus).

It is suitable for connecting to a machine for the application of electro-stimulation and/or for picking up an electromyography signal (EMG), of the known type, and used for example with standard anal probes.

The perineal probe 1 mainly comprise a support rod 2 which constitutes the main portion of the part of the probe 1 to be inserted in the human body and connected to, preferably integral with, a grip 4 of said probe 1. The support rod 2 is substantially cylindrical, that is to say composed of a cylinder having a circular or ellipsoidal base or of other similar analogous form, and is made of insulating material, in particular polymer. The support rod 2 has an outer surface 2a and defines an axial direction 1a, coinciding with the central axis of the probe 1, a circumferential direction 1b and a radial direction 1c.

The support rod 2 preferably has a diameter of 1 cm to 3 cm, a length of 3 cm to 10 cm and borders with an end portion 3, constituting the inner end of the support rod 2, and with the grip 4 positioned on the support rod 2 at the opposite end of the end portion 3.

The perineal probe 1 further comprises a plurality of electrodes 5 positioned on the outer surface 2a of the support rod 2, for electric stimulation and/or surface electromyography detection (EMG).

Advantageously, the probe 1 comprises at least four electrodes 5. Moreover, each electrode 5 extends for a circumferential portion ranging from 60° to 180° (the latter number is appropriately not included in the range), preferably from 70° to 110°, and appropriately for an axial portion preferably comprised between 1 cm and 3 cm.

Appropriately, the electrodes 5 are two by two aligned in an axial direction 1a and reciprocally distanced in a circumferential direction 1b. They are in addition two by two, aligned in a circumferential direction 1b and distanced in an axial direction 1a. Preferably, the distance in an axial direction 1a of two circumferentially aligned electrodes is from 1 mm to 5 mm, in addition the axially aligned electrodes 5 are preferably placed in opposite circumferential positions.

Each electrode 5 is then connected to a different electric output 5a. The electric outputs are electric cables connected to plugs suitable for connection with the sockets present on the machines for the application of electro-stimulation and/or for the detection of impulses.

The applicant has in fact surprisingly discovered that electrodes 5 of the circumferential portions described are suitable to permit a perfectly analogous stimulation to the stimulation achieved with electrodes extending for the entire circumference. Moreover, as described further below, by connecting electrodes 5 in a different manner different functioning modes may be achieved.

The end portion 3 of the perineal probe 1 preferably comprises an inflatable balloon 6 (FIG. 3) extensible beyond the outer surface of the end portion 3. It is connectable to inflation and deflation means of said balloon 6, such as a needle-free syringe. The connections between the balloon and the inflation means are appropriately composed of a hollow channel 6a ending in a hole or aperture, in correspondence with the outer surface of the end portion 3, and with a termination 6b on the opposite side, preferably of the "luer-lock" type, but without ruling out the use of other types of fluid connectors. Inflation is preferably by means of air or even by other gases or even by means of liquids, such as, in particular, water or saline solution or other.

The balloon 6, in a state of rest and thus deflated, preferably covers the end portion 3 and adheres thereto. Diversely, the same balloon 6 inflated (FIG. 3) has the function of stimulating the mechanoreceptors situated at the base of the rectum, simulating faecal content.

The end portion 3 is in addition preferably composed of a separate piece of the support rod 2 firmly connected to the support rod 2 by splicing, gluing, welding or the like. Substantially the end portion 3 is not in a single piece with the support rod 2, thus permitting the manufacturer to easily vary the portion 3, as specified below, to obtain different probes 1 (FIGS. 1-3) maintaining for the vast majority of pieces the same moulds and the same assembly method.

In detail, the end portion 3 may be a substantial continuation of the lateral surface of the support rod 2 without substantial variations of diameter (FIG. 2), so that the perineal probe may be used as a vaginal probe, in particular for treatment of patients with reduced or compromised vaginal access (vaginismus).

Alternatively the end portion 3 has a partially spherical shape cross-sectioned by a transversal plane and not perpendicular to the axial direction 1a (FIG. 1), so as not to interfere with a prostate of increased volume.

The grip 4 of the perineal probe 1 preferably comprises a flattened flexible portion positioned behind the rod 2.

Moreover, near the grip 4, the probe 1 comprises a stop element 7 preferably connectable to the probe, in particular to the rod 2 and/or to the grip 4, in a selectable position in particular in an axial direction 1a. The stop element 7 appropriately comprises a ring 7a engageable on the support rod 2 and/or the grip 4, preferably by means of a bayonet coupling, in a selectable position. Said ring 7a comprises a central recess suitable to permit the adhesion of the anal sphincter thereto. The stop element 7 preferably further comprises, portions 7b projecting in a radial direction 1c, preferably two diametrically opposite portions and each of a length of 2 cm to 4 cm, suitable to obstruct the further insertion of the probe 1.

The functioning of a perineal probe 1, described above in a structural sense, is as follows.

In the production phase, the probe may be manufactured including a partially spherical (FIG. 1), or linear (FIG. 2) end portion 3 and may include the balloon 6 (FIG. 3) or not. Such variations may be made by simply choosing the appropriate end portion 3 to connect to the remaining part of the probe 1.

The probe 1 may be used connecting the electric outputs 5a relative to the single electrodes 5 in a different manner.

For example, by connecting the axially aligned electrodes 5 to the same pole, a bar configuration of electrodes is achieved.

Or by connecting the circumferentially aligned electrodes 5 to the same pole, a loop configuration of electrodes is achieved.

Or even further combinations are possible, for example it is possible to activate only some electrodes and it is possible to use electrodes, entirely or partially, to supply electric impulses and/or for surface electromyography detection (EMG).

Before using the probe 1 it is also important to adjust the position of the stop element 7.

The probe may in addition be used for rectal use with a partially spherical end portion 3 (FIG. 1) or for vaginal use with a linear end portion 3 or the like (FIG. 3). In such latter case it is useful in particular for treatment of patients with reduced or compromised vaginal access.

The invention achieves some important advantages.

In fact, the perineal probe 1 may be used both in the bar and loop conformation.

It allows the patient to purchase a single probe for all purposes.

The probe 1 has, in addition, innovative and advantageous anatomical solutions, such as particular ends 3 and the adjustable grip 4.

Variations may be made to the invention without departing from the scope of the inventive concept expressed in the claims and their technical equivalents.

All details may be replaced with equivalent elements and the materials, shapes and dimensions may be any within the scope of the claims and their technical equivalents.

The invention claimed is:

1. A perineal probe, comprising:
    a support rod comprising an insulating material, defining an axial direction and a circumferential direction,
    an end portion, constituting an inner end of said support rod,
    a grip for said perineal probe connected to said support rod at an end thereof that is opposite from said end portion, and
    exclusively four electrodes positioned on an outer surface of said support rod, each electrode extending for a circumferential portion ranging from 60° to 180° and an axial portion between 1 cm and 3 cm,
    said support rod being cylindrical and having a diameter of 1 cm to 3 cm,
    said electrodes being two by two aligned in said axial direction and reciprocally distanced in a circumferential direction, said electrodes being, in addition, two by two aligned in said circumferential direction and distanced in an axial direction, and each of said electrodes being connected to a different electric output,
    the distance in said axial direction of two circumferentially aligned of said electrodes is from 1 mm to 5 mm.

2. The perineal probe according to claim 1, wherein said end portion is a substantial continuation of the lateral surface of said support rod without substantial variations of diameter, so that said perineal probe may be used as a vaginal probe.

3. The perineal probe according to claim 1, wherein said end portion has a partially spherical shape cross-sectioned by a transversal plane and not perpendicular to said axial direction.

4. The perineal probe according to claim 1, wherein each electrode extends from a circumferential portion ranging from 70° to 110°.

5. The perineal probe according to claim 1, wherein said end portion is a separate piece of said support rod and is firmly connected to said support rod.

6. The perineal probe according to claim 1, further comprising a stop element connected to the support rod, the stop element comprising portions projecting in a radial direction, configured to obstruct the further insertion of said probe.

7. The perineal probe according to claim 1, further comprising a stop element that is connected to the support rod and adjustable in an axial direction.

8. The perineal probe according to claim 1, wherein said end portion comprises an inflatable balloon extensible beyond the outer surface of said end portion.

9. The perineal probe according to claim 8, wherein said inflatable balloon is connected to an inflation and deflation means of said inflatable balloon.

\* \* \* \* \*